United States Patent [19]

Irick, Jr. et al.

[11] Patent Number: 5,011,806

[45] Date of Patent: Apr. 30, 1991

[54] CATALYST COMPOSITION FOR THE HYDROGENATION OF CARBOXYLIC ACID ESTERS

[75] Inventors: Gether Irick, Jr., Gray; Patricia N. Mercer, Kingsport; Kenneth E. Simmons, Blountville, all of Tenn.

[73] Assignee: Eastman Kodak Company, Rochester, N.Y.

[21] Appl. No.: 474,920

[22] Filed: Feb. 5, 1990

Related U.S. Application Data

[62] Division of Ser. No. 309,641, Feb. 13, 1989, Pat. No. 4,929,777.

[51] Int. Cl.$^5$ .................. B01J 21/06; B01J 23/06; B01J 23/10; B01J 23/72
[52] U.S. Cl. ..................... 502/202; 502/243; 502/303; 502/342; 502/343
[58] Field of Search ............... 502/242, 303, 343, 345, 502/346, 350, 202, 342

[56] References Cited

U.S. PATENT DOCUMENTS 4,085,193 4/1978 Nakajima et al. .............. 502/242 X

FOREIGN PATENT DOCUMENTS 53-2405 1/1978 Japan .................................. 502/345

Primary Examiner—W. J. Shine
Attorney, Agent, or Firm—J. Frederick Thomsen; William P. Heath, Jr.

[57] ABSTRACT

Disclosed are catalyst compositions comprised of chemically-mixed, copper-titanium oxides and the use of such catalyst compositions in the hydrogenation of certain esters to obtain the alcohol corresponding to the acid residue of the ester.

5 Claims, No Drawings

CATALYST COMPOSITION FOR THE HYDROGENATION OF CARBOXYLIC ACID ESTERS

This is a divisional of copending application Ser. No. 07/309,641 filed on Feb. 13, 1989, now U.S. Pat. No. 4,929,777.

This invention concerns certain novel chemically-mixed, copper-titanium oxide catalysts and the use of such catalysts in hydrogenating carboxylic acid esters to the alcohol which is analagous to the carboxylic acid portion of the ester.

Processes for the hydrogenation of carboxylic acid esters (referred to herein simply as esters) to alcohols is of significant commercial importance. For example, dimethyl succinate can be hydrogenated to 1,4-butanediol and dimethyl 1,4-cyclohexanedicarboxylate can be hydrogenated to 1,4-cyclohexanedimethanol. Both of these diols are used in substantial quantities in the manufacture of polyesters from which various molded articles and fibers are made. Another example is the manufacture of long chain alcohols by the hydrogenation of natural fats, i.e., glyceryl esters of long chain fatty acids.

Catalysts normally used in the hydrogenation of esters to produce alcohols generally require extremely high pressures, e.g., greater than 4000 pounds per square inch (psi), to achieve commercially-feasible rates of conversion to the desired alcohol. The most commonly employed catalyst in such hydrogenations is copper chromite.

We have discovered that chemically-mixed, copper-titanium oxide compositions are superior catalysts in processes for hydrogenating esters to alcohols. These catalytic compositions represent a substantial improvement over known ester hydrogenation catalysts in that they catalyze the hydrogenation of esters at satisfactory conversion rates and selectivity at pressures significantly below 4000 psi, typically below 2500 psi. Moreover, our novel catalyst compositions do not contain toxic metals such as nickel or chromium and thus they are safer to manufacture and present fewer environmental problems and occupational hazards in their use and disposal.

The catalyst compositions provided by this invention comprise chemically-mixed, copper-titanium oxides, i.e., a composition which contains —Ti—O—Cu— bonds. These chemically-mixed oxide compositions may contain from 1 to about 75 weight percent copper oxide (calculated as CuO). However, catalytic activity for ester hydrogenation, especially when using the preferred conditions of temperature and pressure as described hereinbelow, is unsatisfactory when the copper oxide content of the compositions is below about 3, or above about 65, weight percent. Consequently, the copper oxide content of our novel catalyst compositions normally will be in the range of about 3 to 65 weight percent, based on the weight of the chemically-mixed, copper-titanium oxides. The preferred compositions contain about about 8.8 to 44.0 weight percent copper oxide (same basis).

The essential ingredient, i.e., the chemically-mixed, copper-titanium oxides, of the novel catalyst compositions may be further defined by the formula $Cu_xTi_yO_z$ wherein x, y, and z represent atomic ratios and x is about 0.01 to 0.75, y is about 0.99 to 0.25 and z is about 1.99 to 1.25. The particularly preferred catalyst compositions are those wherein x is about 0.09 to 0.44, y is about 0.91 to 0.56 and z is about 1.91 to 1.56.

In addition to the mixed copper-titanium oxides, the catalyst compositions may contain or be deposited on or in other materials. As our catalysts are developed for use in specific process, it may be advantageous to add minor amounts, e.g., up to about 10 weight percent, of other elements such as Li, Na, K, Rb, Cs, Mg, Ca, Sr, Ba, La, Ce or possibly others to the catalyst compositions to increase their lifetimes in commercial operations or to modify their activity and selectivity. It also may be desirable to add "structural promoters" to the catalysts to increase surface area or to change the acidity/basicity to optimize performance of the catalyst in a specific process. Such structural promoters as the oxides of silicon, aluminum, germanium, boron, tin, zinc etc. can be combined with the catalysts during their preparation, replacing part of the titanium component but maintaining the concentration of the copper oxide in the catalysts, which may also contain an oxide of lanthanum or zinc, within the range of about 3 to 65 weight percent. Alternatively, the catalysts may be deposited on such oxides, for example, by preparing the catalysts in the presence of such an oxide of a particular shape or particle size.

Our novel catalyst compositions can be used in the form of powders, cylinders, spheres, honeycombs, etc., the physical form being dictated by the type of reactor chosen for and by economic and engineering considerations associated with a particular hydrogenation process. Frequently, it will be desirable to use a binder to assist in the formation and maintenance of the catalyst compositions in a particular shape. For example, alumina, clays and zirconia are commonly used binders in the manufacture of commercial catalyst pellets or cylinders.

The catalyst compositions of this invention may be prepared by a variety of methods. Generally, suitable procedures are described in Volumes 1 and 3 of Studies in Surface Science and Catalysis, Elsevier Scientific Publishing Company. The source of the titanium component of our catalysts may be titanium tetrachloride, tetraisopropyl titanate, titania sol, titanium bromide, titanium butoxide, titanium methoxide, titanium butoxybis-(2,4-pentanedionate), titanium oxides, etc. Compounds which may be used as the source of the copper component include copper chloride, copper bromide, copper acetate, copper ethoxide, copper hydroxide, copper nitrate, copper gluconate, copper pentanedionate, copper oxides, etc.

The titanium and copper compounds may be physically mixed, heated in air at temperatures above 500° C., ground and then reheated. Where appropriate, hydrous titania can be precipitated and treated with a soluble copper salt such as a chloride, bromide, acetate or nitrate followed by drying and calcining in air at 550° C. Another procedure comprises coating a soluble copper compound onto the surface of an amorphous form of titanium oxide (hydrous oxide), followed by calcining in air. The exact method of preparation is not critical so long as the formation of —Ti—O—Cu— is achieved. This bonding distinguishes the essential or active ingredient of our catalysts from those in which copper is merely deposited on the surface of a support and exists primarily as a —Cu—O—Cu— species. Other elements or compounds, such as those specified hereinabove, may be added to the titanium and copper sources during preparation of the catalyst.

The esters which may be hydrogenated in accordance with the process provided by this invention are aliphatic, cycloaliphatic and aromatic esters of aliphatic and cycloaliphatic mono- and poly-carboxylic acids. The carboxylic acid residue of the ester reactants is not important to our process provided that each oxycarbonyl group hydrogenated is bonded to an aliphatic or cycloaliphatic carbon atom. For example, esters of arylcarboxylic acids such as alkyl benzoates are not included in the ester reactants in our process whereas esters of aralkylcarboxyl acids such as alkyl phenylacetates are included within the meaning of esters of aliphatic acids. The aliphatic acid residues may be straight- or branched-chain, saturated or unsaturated and unsubstituted or substituted, for example with a wide variety of substituents such as halogen, hydroxy, alkoxy, amino, substituted amino, acylamido, aryl, cycloalkyl, etc. The main chain of the aliphatic acid residues may contain hetero atoms such as oxygen, sulfur and nitrogen atoms.

Typically, the ester reactants employed in our process may contain up to about 40 carbon atoms. Examples of the carboxylic acid esters include the aliphatic, cycloaliphatic and aromatic esters of acetic, propionic, butyric, valeric, hexanoic, heptanoic, octanoic, nonanoic, decanoic, undecanoic, lauric, tridecanoic, myristic, pentadecanoic, palmitic, heptadecanoic, stearic, oleic, linoleic, linolenic, nonadecanoic, eicosanoic, arachidonic, heneicosanoic, docosanoic, tetracosanoic, octacosanoic, triacontanoic, dotriacontanoic, acrylic, methacrylic, crotonic, 3-butenoic, cyclobutanecarboxylic, 2-norbornanecarboxylic, malonic, succinic, glutaric, maleic, glutaconic, adipic, pimelic, suberic, azelaic, sebacic, 1,2,4-hexanetricarboxylic, 1,2-, 1,3-, and 1,4-cyclohexanedi- carboxylic, 2,6- and 2,7-octahydronaphthalenedicarboxylic, 3-[(2-carboxyethyl)thio]butyric, etc. The alcohol segment of the ester reactants may be the residue of any mono- or poly-hydroxy compound such as methanol, ethanol, butanol, 2-butanol, 2-ethyl-hexanol, 2,2-dimethyl-1,3-propanediol, ethylene glycol, propylene glycol, 1,4-butanediol, 1,6-hexanediol, 1,10-decanediol, cyclohexanol, benzyl alcohol, diethylene glycol, glycerin, trimethylolpropane, phenol, hydroquinone, etc. The hydrogenation process provided by our invention is particularly useful for converting lower, i.e., $C_1$–$C_4$, alkyl esters, especially methyl esters, of $C_{10}$–$C_{20}$ carboxylic acids and cyclohexanedicarboxylic acids, e.g., dimethyl 1,4-cyclohexanedi- carboxylic acid.

The amount of catalyst required can be varied substantially depending on a number of factors such as, for example, the composition of the catalyst and the hydrogenation conditions being used. Furthermore, in certain modes of operation such as trickle bed or vapor phase processes using a fixed bed of catalyst, the amount of catalyst present relative to the ester reactant is difficult to define with any degree of precision.

The hydrogenation conditions of pressure and temperature also can be varied depending not only on one another but also the activity of the catalyst, the mode of operation, selectivity considerations and the desired rate of conversion. Esters may be hydrogenated to their corresponding alcohols according to our novel process using temperatures in the range of about 150° to 350° C. and hydrogen pressures in the range of about 500 to 6000 psi. However, since hydrogenation rates generally increase with temperature, it is normally desirable to operate in the range of about 200° to 300° C. range to maximize both conversion rates and utilization of the commercial hydrogenation facility. While rates and conversions generally also increase with increasing pressure, the energy costs for compression of hydrogen, as well as the increased cost of high-pressure equipment render the use of the lowest pressure practical very advantageous. Thus, a highly attractive feature of our novel process is the use of hydrogen pressures below 3000 psi, especially in the range of about 600 to 2000 psi, which give good rates of conversion, especially when used in conjunction with a hydrogenation temperature in the range of about 250° to 300° C.

The ester hydrogenation process of this invention may be carried out in the absence or presence of an inert solvent, i.e., a solvent for the ester being hydrogenated which does not affect significantly the activity of the catalyst and does not react with the hydrogenation product or products. Examples of such solvents include alcohols such as ethanol and lauryl alcohol; glycols such as mono-, di- and tri-ethylene glycol; hydrocarbons such as hexane, cyclohexane, octane and decane; and aromatic ethers such as diphenyl ether, etc.

The hydrogenation process may be carried out as a batch, semi-continuous or continuous process. In batch operation a slurry of the catalyst in the reactant and/or an inert solvent in which the reactant has been dissolved is fed to a pressure vessel equipped with means for agitation. The pressure vessel then is pressurized with hydrogen to a predetermined pressure followed by heating to bring the reaction mixture to the desired temperature. After the hydrogenation is complete the reaction mixture is removed from the pressure vessel, the catalyst is separated by filtration and the product is isolated, for example, in a distillation train.

Continuous operation can utilize a fixed bed using a larger particle size of catalyst, e.g., catalyst pellets. The catalyst bed may be fixed in a tubular or columnar, high pressure reactor and the liquid reactant, dissolved in an inert solvent if necessary or desired, slowly fed continuously above the bed at elevated pressure and temperature and crude product removed from the base of the reactor. Alternatively, the described fixed-bed catalyst system may be used in a gas-phase mode of operation wherein a reactant, which is sufficiently volatile under the hydrogenation conditions, is vaporized and passed through the catalyst bed, the off-gas is condensed and the product is isolated. Another mode of continuous operation utilizes a slurry of the catalyst in an agitated pressure vessel which is equipped with a filter leg to permit continuous removal of a solution of product in unreacted ester and/or an inert solvent. In this manner a liquid reactant or reactant solution can be continuously fed to and product solution continuously removed from an agitated pressure vessel containing an agitated slurry of the catalyst.

Our novel catalyst compositions and hydrogenation process are further illustrated by the following examples.

PREPARATION OF CATALYST COMPOSITIONS

EXAMPLE 1

Titanium tetraisopropoxide (172.1 g, 0.61 mol) was added dropwise to 500 mL water with rapid stirring. After the addition was complete, the slurry was stirred an additional hour. The solid was filtered and washed by reslurrying in water and filtering a second time. The solid was then reslurried in about 500 mL of water and the pH was adjusted to 10 with concentrated ammonium hydroxide. The slurry then was heated, with stirring, to and held at 60° C. for three hours. The slurry was cooled with stirring and filtered. The solids collected were added with stirring to a solution of copper (I) acetate (10.26 g, 0.08 mol) in 450 mL water. The resulting slurry was heated, with stirring, to and held at 60° C. for three hours. The slurry was cooled to room temperature with stirring and then filtered and washed on the filter with water. The solid material collected was dried on a steam bath and then calcined in air for one hour at 200° C., one hour at 350° C. and three hours at 550° C. The catalyst composition thus obtained contained 8.8 weight percent copper, had a BET surface area of 9 square meters per g ($m^2/g$) and had the formula $Cu_{0.11}Ti_{0.89}O_{1.89}$.

EXAMPLE 2

Titanium tetraisopropoxide (71.2 g, 0.25 mol) was added dropwise to 500 mL water with rapid stirring. After the addition was complete, the slurry was stirred an additional hour. The solid was filtered and washed once by reslurrying in water and filtering a second time. The solid was then reslurried in about 500 mL of water and the pH was adjusted to 10 by adding concentrated ammonium hydroxide dropwise with stirring. The slurry then was heated, with stirring, to and held at 60° C. for three hours. The slurry was cooled with stirring and filtered. The solids collected were added with stirring to a solution of cupric acetate (6.3 g, 0.03 mol) in 500 mL water. The resulting slurry was heated, with stirring, to and held at 60° C. for three hours. The slurry was cooled to room temperature with stirring and then filtered and washed on the filter with water. The solid material collected was dried on a steam bath and then calcined in air for one hour at 200° C., one hour at 350° C. and three hours at 550° C. The catalyst composition thus obtained contained 9.4 weight percent copper, had a BET surface area of 12.4 $m^2/g$ and had the formula $Cu_{0.12}Ti_{0.88}O_{1.88}$.

EXAMPLE 3

Example 2 was repeated using 4.34 g (0.024 mol) of cupric acetate to obtain a catalyst composition containing 6.6 weight percent copper. The catalyst had a BET surface area of 11.7 $m^2/g$ and the formula $Cu_{0.08}Ti_{0.92}O_{1.92}$.

EXAMPLE 4

Example 2 was repeated using 3.14 g (0.017 mol) of cupric acetate to obtain a catalyst composition containing 5.0 weight percent copper. The catalyst had a BET surface area of 7.7 $m^2/g$ and the formula $Cu_{0.06}Ti_{0.94}O_{1.94}$.

EXAMPLE 5

Example 2 was repeated using 1.89 g (0.010 mol) of cupric acetate to obtain a catalyst composition containing 3.1 weight percent copper. The catalyst had a BET surface area of 13.6 $m^2/g$ and the formula $Cu_{0.04}Ti_{0.96}O_{1.96}$.

EXAMPLE 6

Example 2 was repeated using 0.63 g (0.003 mol) of cupric acetate to obtain a catalyst composition containing 1.1 weight percent copper. The catalyst had a BET surface area of 11.8 $m^2/g$ and the formula $Cu_{0.02}Ti_{0.98}O_{1.98}$.

EXAMPLE 7

To 100 g silica (Davison 59) was added a solution of 71.2 g titanium tetraisopropoxide in 300 mL of 2-propanol. The mixture was stirred and heated at 60° C. until all of the 2-propanol was removed. To the resulting solid was added over 10 minutes a solution of 37.7 g cupric acetate in 800 mL of 60° C. water. The mixture was stirred and evaporated to dryness on a steam bath and the solid obtained was calcined for one hour at 200° C., for one hour at 350° C. and for three hours at 550° C. to give a black catalyst. The catalyst composition contained 34 weight percent copper, had a BET surface area of 222 $m^2/g$ and consisted of $Cu_{0.43}Ti_{0.57}O_{1.57}$ coated on silica.

EXAMPLE 8

A mixture of 51.2 g silica (Davidson Grade 59) and 106.8 g titanium tetraisopropoxide was heated on a steam bath for one hour with stirring to give a white solid to which was added a solution of 47.13 g of cupric acetate monohydrate in 1 L of 60° C. water. The resulting slurry was evaporated to dryness and calcined according to the procedure described in Example 7. The catalyst composition thus obtained was a brown-black, contained 31 weight percent copper, had a BET surface area of 183 $m^2/g$ and consisted of $Cu_{0.39}Ti_{0.61}O_{1.61}$ coated on silica.

EXAMPLE 9

To a solution of 34.5 g cupric acetate monohydrate and 8.5 g lanthanum acetate.1½$H_2O$ in 2 L water was added in two minutes 356 g titanium tetraisopropoxide. The slurry was stirred for 30 minutes and the pH adjusted to 7.0 with concentrated ammonium hydroxide. The slurry then was heated, with stirring, to and held at 60° C. for 90 minutes and cooled to 25° C. in two hours. The slurry then was filtered and the green solid collected was dried on a steam bath in air followed by calcining according to the procedure described in Example 7. The dark brown-black catalyst composition contained 9.3 weight percent copper and 2.9 weight percent lanthanum, had a BET surface area of 51.9 $m^2/g$ and consisted of $La_{0.02}Cu_{0.12}Ti_{0.86}O_{1.87}$.

EXAMPLE 10

To a solution of 59.52 g cupric acetate monohydrate and 4.25 g lanthanum acetate.1½$H_2O$ in 1 L water was added in five minutes 176 g titanium tetraisopropoxide. The mixture was cooled to 25° C. with stirring and the pH adjusted to 7.0 with concentrated ammonium hydroxide. The slurry then was filtered and the green solid collected was dried on a steam bath in air followed by calcining according to the procedure described in Example 7. The black catalyst composition contained 23.7 weight percent copper and 2.3 weight percent lanthanum, had a BET surface area of 13.1 $m^2/g$ and consisted of $La_{0.02}Cu_{0.30}Ti_{0.68}O_{1.69}$.

EXAMPLE 11

Titanium tetraisopropoxide (44.5 g) was added in five minutes to 300 mL water and the resulting slurry was stirred for ten minutes and heated to 60° C. To the slurry was added 53.6 g powdered cupric acetate monohydrate and the mixture was stirred at 60° C. while the pH was adjusted to 10.0 with concentrated ammonium hydroxide. The mixture was stirred for 15 minutes at 60° C. and then evaporated to dryness. The solid obtained was calcined as described in Example 7 to give a black catalyst composition containing 50.4 weight percent copper and having the formula $Cu_{0.63}Ti_{0.37}O_{1.37}$.

EXAMPLE 12

Titanium tetraisopropoxide (26.6) was added to 300 mL water in fifteen minutes and the slurry was stirred for one hour. The solids were filtered off, reslurried in 300 mL water, filtered again and then reslurried in 300 mL water. After the pH was adjusted to 10.0, the slurry was stirred and heated at 60° C. for three hours, then cooled to 25° C. and filtered. The solids collected were added to a solution of 31.42 g cupric acetate in 500 mL water. The mixture was heated to 60° C. and stirred at that temperature for three hours. The mixture was then cooled to 25° C., filtered and the solids obtained were washed with 50 mL water. The solid material was dried and calcined according to the procedure described in Example 7. The black catalyst composition thus obtained contained 25.2 weight percent copper, had a BET surface area of 6.3 m²/g and had the formula $Cu_{0.32}Ti_{0.68}O_{1.68}$.

EXAMPLE 13

Example 2 was repeated using 356 g of titanium isopropoxide and 34.5 g (0.024 mol) of cupric acetate to obtain a catalyst composition containing 9.6 weight percent copper. This catalyst had a BET surface area of 11.3 m²/g and the formula $Cu_{0.12}Ti_{0.88}O_{1.88}$.

EXAMPLE 14

Calcium acetate (0.42 g, 0.002 mol) was dissolved in 10 mL of water. To this solution was added 5.0 g of the catalyst of Example 13 with stirring. This slurry was stirred at 60° C. for five minutes and then was evaporated to dryness on a steam bath. The solids obtained were calcined in air at 300° C. for three hours. The catalyst thus obtained had a surface area of 11.2 m²/g.

EXAMPLE 15

Example 14 was repeated using magnesium acetate (0.85 g, 0.004 mol) instead of calcium acetate. The resulting catalyst had a surface area of 10.3 m²/g.

EXAMPLE 16

Example 14 was repeated using potassium acetate (0.24 g, 0.002 mol) instead of calcium acetate. The resulting catalyst had a surface area of 10.0 m²/g.

EXAMPLE 17

Example 14 was repeated using lanthanum acetate (0.29 g, 0.001 mol) instead of calcium acetate. The resulting catalyst had a surface area of 12.0 m²/g.

EXAMPLE 18

To 20.0 g of silica (Davison Grade 57) was added 41.6 g (0.15 mol) titanium tetraisopropoxide. The resulting slurry was heated on a steam bath to give a white solid. A solution of 13.42 g (0.07 mol) of cupric acetate in 500 mL of 60° C. water was added to the solid and the mixture was evaporated to dryness on a steam bath. The solid was calcined for one hour at 200° C., one hour at 250° C. and three hours at 550° C. The resulting catalyst had a surface area of 182 m²/g and consisted of $Cu_{0.31}Ti_{0.69}O_{1.69}$.

EXAMPLE 19

The procedure described in Example 18 was repeated using 51.2 g of silica (Davison Grade 57), 106.8 g (0.38 mol) of titanium tetraisopropoxide and 47.13 g (0.24 mol) of cupric acetate. This procedure was performed five times and the resulting calcined solids were combined to give a large batch of material. This catalyst had a surface area of 186 m²/g and consisted of $Cu_{0.39}Ti_{0.61}O_{1.61}$.

HYDROGENATION OF ESTERS

Example 20–25 describe the liquid phase hydrogenation of dimethyl succinate (10.0 g) in methanol (100 mL) in the presence of one of the catalysts prepared as described hereinabove. The hydrogenations were conducted in an autoclave equipped with a 300 mL glass liner, a stir fin, thermometer, pressure gauge, a gas inlet tube and means for heating and cooling the autoclave. In each hydrogenation procedure, the methanol, dimethyl succinate and the chemically-mixed, copper-titanium oxide catalyst were charged to the glass liner which was positioned within the autoclave. The autoclave was first pressurized to 500 psi with nitrogen and vented and then pressurized to 2000 psi with hydrogen. Stirring was started and the autoclave was heated to 200° C. (Example 20) or 300° C. (Example 21-25) at the maximum heating rate. The contents of the autoclave were stirred at 200° C. (Example 20) or 300° C. (Examples 21-25) and 2000 psi for five hours and then the autoclave was cooled and vented carefully to avoid the loss of any of the contents.

EXAMPLE 20

Using the above-described procedure, dimethyl succinate was hydrogenated at 2000 psi hydrogen and 200° C. for five hours in the presence of 1.0 g of the catalyst obtained in Example 1. Analysis of the reaction mixture obtained showed 2.4 percent butyrolactone and 11.2 percent 1,4-butanediol.

EXAMPLE 21

Example 20 was repeated using a hydrogenation temperature of 300° C. to produce a crude product which contained 10.7 percent butyrolactone and 23.3 percent 1,4-butanediol.

EXAMPLE 22

Example 21 was repeated using 1.0 g of a catalyst prepared by repeating the catalyst synthesis procedure described in Example 1. The resulting reaction mixture contained 14.1 percent tetrahydrofuran, 3.2 percent butyrolactone and 20.0 percent 1,4-butanediol.

EXAMPLE 23

Example 21 was repeated using 1.0 g of the catalyst prepared in Example 2. The resulting reaction mixture contained 13.2 percent tetrahydrofuran, 4.9 percent butyrolactone and 23.9 percent 1,4-butanediol.

EXAMPLE 24

Example 21 was repeated using 1.0 g of the catalyst prepared as described in Example 3. The resulting reaction mixture contained 13.4 percent tetrahydrofuran, 4.5 percent butyrolactone and 15.1 percent 1,4-butanediol.

EXAMPLE 25

Example 21 was repeated using 1.0 g of the catalyst prepared in Example 4. The resulting reaction mixture contained 6.3 percent tetrahydrofuran, 5.2 percent butyrolactone and 10.5 percent 1,4-butanediol.

Examples 26–68 describe the results obtained from the gas-phase hydrogenation of methyl acetate using the catalysts provided by our invention and varying gas flow rates, temperatures and pressures. The apparatus used consisted of a ¼-inch interior diameter, stainless steel, tubular reactor in which was placed 1 mL (approximately 1 g) of catalyst held in place with quartz wool plugs above and below the catalyst bed. The central portion of the tube was encased in an electric furnace with a thermocouple fixed in the catalyst bed. Hydrogen and methyl acetate vapor were fed, using Brooks flow controllers, to the top of the reactor in a hydrogen:methyl acetate mole ratio of 3:1 and 6:1. The pressure of the off-gas removed from the bottom of the reactor was reduced to atmospheric pressure, cooled in a glycol condenser system and the resulting liquid and gas phases were analyzed by gas chromatography. The results obtained in Examples 26–68 are given in the Table. The numerical designation for the catalyst (Cat) used in each example refers to the example which describes its preparation. Temperature (Temp) and total pressure (Press) are given in °C. and pounds per square inch absolute, respectively. Gas flow rates are given as the gas hourly space velocity (GHSV) which is the mL of gas fed per hour divided by the mL of catalyst bed. The % methyl acetate (MeOAc) designates the mole percent of methyl acetate which is not converted to other compounds. The conversion rates to methanol (MeOH), ethanol (EtOH) and ethyl acetate (EtOAc) are given in micromoles per g catalyst per second.

TABLE

| Ex. | Cat. | Temp. | Press | GHSV | % MeOAc | Rate of Conversion to | | |
|---|---|---|---|---|---|---|---|---|
| | | | | | | MeOH | EtOH | EtoAc |
| 26 | 1 | 231 | 740 | 32067 | 60.5 | 3.1 | 1.4 | 2 |
| 27 | 1 | 251 | 775 | 32067 | 42.2 | 4.9 | 2.1 | 2.8 |
| 28 | 1 | 278 | 775 | 32067 | 56 | 10 | 4.3 | 5.1 |
| 29 | 1 | 297 | 800 | 29343 | 44.8 | 8.2 | 2.8 | 5.2 |
| 30 | 1 | 306 | 780 | 29343 | 9.2 | 8 | 3 | 5.4 |
| 31 | 1 | 306 | 800 | 28256 | 45.77 | 7.99 | 3.06 | 5.1 |
| 32 | 1 | 288 | 765 | 25660 | 57.9 | 11.8 | 6.4 | 3.9 |
| 33 | 13 | 247 | 760 | 28784 | 25.6 | 4.6 | 1.6 | 2 |
| 34 | 13 | 276 | 765 | 28502 | 34.4 | 10.5 | 4.9 | 4.8 |
| 35 | 7 | 278 | 770 | 28226 | 36.6 | 27.9 | 8.7 | 12.2 |
| 36 | 12 | 246 | 790 | 28179 | 23 | 5.8 | 3 | 2 |
| 37 | 12 | 277 | 830 | 28226 | 39.3 | 18.4 | 9.1 | 6.1 |
| 38 | 12 | 303 | 815 | 28502 | 50.6 | 28.7 | 16.2 | 8.4 |
| 39 | 12 | 242 | 780 | 16350 | 46.8 | 10.8 | 7.8 | 3.6 |
| 40 | 12 | 279 | 790 | 16632 | 32.2 | 17.4 | 7.3 | 6.7 |
| 41 | 5 | 245 | 800 | 28502 | 22.1 | 3.8 | 1.4 | 1.7 |
| 42 | 5 | 270 | 790 | 28502 | 33.8 | 8.3 | 3.3 | 3.9 |
| 43 | 9 | 249 | 760 | 28502 | 42.5 | 13.5 | 5.7 | 5.5 |
| 44 | 9 | 287 | 760 | 28502 | 69.4 | 31.3 | 21.4 | 7.7 |
| 45 | 8 | 252 | 745 | 28226 | 35.5 | 22.6 | 7 | 10.6 |
| 46 | 8 | 287 | 725 | 28502 | 60.7 | 56.3 | 33.8 | 16 |
| 47 | 10 | 247 | 810 | 28824 | 41.8 | 6.1 | 4 | 5.4 |
| 48 | 10 | 283 | 800 | 28224 | 80.7 | 23.1 | 32.5 | 9 |
| 49 | 18 | 263 | 765 | 27942 | 54.8 | 11.8 | 8.3 | 11.3 |
| 50 | 18 | 292 | 750 | 27942 | 72.8 | 22.3 | 27.9 | 12.7 |
| 51 | 18 | 274 | 795 | 16074 | 50 | 12.9 | 10.7 | 14.2 |
| 52 | 14 | 249 | 770 | 27942 | 30 | 1.8 | 1.4 | 1.3 |
| 53 | 14 | 275 | 775 | 28224 | 45.9 | 3.8 | 3 | 3.9 |
| 54 | 14 | 248 | 750 | 27102 | 47.4 | 1.8 | 0.8 | 0.5 |
| 55 | 17 | 292 | 750 | 27104 | 61.2 | 10.4 | 6.4 | 2.5 |
| 56 | 19 | 248 | 750 | 27384 | 39 | 10.5 | 2.8 | 4.4 |
| 57 | 19 | 281 | 760 | 27384 | 58.9 | 24.9 | 13.9 | 6.8 |
| 58 | 19 | 252 | 760 | 14676 | 33.6 | 10.5 | 2.7 | 4 |
| 59 | 19 | 280 | 750 | 14952 | 38.2 | 23.5 | 10.3 | 7.7 |
| 60 | 15 | 242 | 750 | 27384 | 27.5 | 1.4 | 0.9 | 0.1 |
| 61 | 15 | 279 | 750 | 27384 | 35.5 | 6.3 | 3.6 | 1.7 |
| 62 | 15 | 280 | 740 | 15234 | 26.2 | 3.4 | 1.9 | 0.8 |
| 63 | 16 | 244 | 750 | 27384 | 21 | 0.7 | 0.2 | 0.1 |
| 64 | 16 | 280 | 760 | 27384 | 19.3 | 1.1 | 0.6 | 0.1 |
| 65 | 16 | 295 | 750 | 15234 | 22.5 | 1.6 | 1 | 0.1 |
| 66 | 14 | 247 | 740 | 27384 | 28.4 | 3.5 | 1.7 | 1 |
| 67 | 14 | 283 | 740 | 27384 | 50.3 | 13.2 | 8.1 | 3.4 |
| 68 | 14 | 276 | 740 | 15234 | 36.9 | 9 | 4.4 | 2.6 |

The invention has been described in detail with particular reference to preferred embodiments thereof, but it will be understood that variations and modifications will be effected within the spirit and scope of the invention.

What is claimed is:

1. A catalyst composition comprising as the essential ingredients chemically-mixed, copper-titanium oxide which contains —Ti—O—Cu— bonds wherein the copper oxide content, calculated as CuO, of the catalyst composition is from about 3 to 65 weight percent and an oxide of lanthanum or zinc.

2. A catalyst composition according to claim 1 wherein the copper oxide content, calculated as CuO, of the catalyst composition is from about 8.8 to 44.0 weight percent.

3. A catalyst composition comprising as the essential ingredients chemically-mixed, copper-titanium oxide of the formula $Cu_xTi_yO_z$ wherein x, y, and z represent atomic ratios and x is about 0.01 to 0.75, y is about 0.99 to 0.25, and z is about 1.99 to 1.25 and an oxide of lanthanum or zinc.

4. A catalyst composition according to claim 3 wherein x is about 0.09 to 0.44, y is about 0.91 to 0.56 and z is about 1.91 to 1.56.

5. A catalyst composition according to claim 4 combined with or deposited on an oxide of silicon, aluminum, germanium, boron, or tin.

* * * * *